(12) United States Patent
Burkart et al.

(10) Patent No.: US 11,931,045 B2
(45) Date of Patent: Mar. 19, 2024

(54) SIMPLIFIED FIELD USE JUNCTIONAL TOURNIQUETS

(71) Applicant: The United States of America, as represented by the Secretary of the Navy, Crane, IN (US)

(72) Inventors: Joseph Thomas Burkart, Bloomfield, IN (US); Danielle E. Cafasso, Southern Pines, NC (US); Robert Henry Hayford, Colorado Springs, CO (US); Huckelberry Finne, Norfolk, VA (US); Jose Ramirez Vargas, Clovis, NM (US); Michael P Abbott, Chesapeake, VA (US)

(73) Assignee: The United States of America, Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 17/570,680

(22) Filed: Jan. 7, 2022

(65) Prior Publication Data
US 2022/0125437 A1 Apr. 28, 2022

Related U.S. Application Data

(62) Division of application No. 16/593,389, filed on Oct. 4, 2019, now Pat. No. 11,253,268.

(51) Int. Cl.
*A61B 17/132* (2006.01)
(52) U.S. Cl.
CPC ...... *A61B 17/1325* (2013.01); *A61B 17/1327* (2013.01)

(58) Field of Classification Search
CPC ............ A61B 17/1325; A61B 17/1327; A61B 17/1322; A61B 17/132; A44C 5/0053; A44C 5/18; A44C 5/2042; A44C 5/2057; A44C 5/208; A44B 11/003; A44B 11/005; A44B 11/006; A44B 11/02; A44B 11/065; A44B 11/12; A44B 11/125; A61F 5/30; A61F 5/37; A61F 5/0048; A61F 2002/7862; A61F 2002/30462; A61F 5/449; A61F 2007/0228; A61F 13/56; A61F 13/64; A61F 13/62; A61F 13/622
(Continued)

(56) References Cited

U.S. PATENT DOCUMENTS 10,363,198 B2 * 7/2019 Salstein-Begley ..... A61H 39/04
2004/0122469 A1 * 6/2004 Akerfeldt ........... A61B 17/1325
606/201

(Continued)

*Primary Examiner* — Wade Miles
*Assistant Examiner* — Bridget E. Rabaglia
(74) *Attorney, Agent, or Firm* — Naval Surface Warfare Center, Crane Division; Christopher Feigenbutz

(57) ABSTRACT

A junctional tourniquet apparatus and related methods of use. An exemplary tourniquet has an inverted cone shape, wherein a narrower end has a mushroom shaped base that is pressed against a compression target and a broader end has a plurality of pass-through slots for straps. Another exemplary tourniquet has a broad plate component and a handle component. The handle component has a mushroom shaped base on a first end and a handle on a second end. The handle component passes through the center of the plate component with threads that allow the handle component to compress a target by twisting the handle.

8 Claims, 11 Drawing Sheets

(58) Field of Classification Search
USPC .................................................. 606/203, 204
See application file for complete search history.

(56) References Cited

U.S. PATENT DOCUMENTS

| | | | |
|---|---|---|---|
| 2010/0152770 A1* | 6/2010 | Spencer | A61B 17/1325 606/203 |
| 2012/0150215 A1* | 6/2012 | Donald | A61B 17/1325 606/203 |
| 2016/0058130 A1* | 3/2016 | Boney | A43B 3/36 24/712.6 |
| 2018/0193030 A1* | 7/2018 | Ward | A61B 17/1325 |

* cited by examiner

SIMPLIFIED FIELD USE JUNCTIONAL TOURNIQUETS

CROSS-REFERENCE TO RELATED APPLICATIONS

This application is a divisional of U.S. patent application Ser. No. 16/593,389, filed Oct. 4, 2019, entitled "SIMPLIFIED FIELD USE JUNCTIONAL TOURNIQUET," which claims priority to U.S. Provisional Patent Application Ser. No. 62/741,176 filed Oct. 4, 2018 entitled "SIMPLIFIED FIELD USE JUNCTIONAL TOURNIQUET," the disclosure of which is expressly incorporated by reference herein.

STATEMENT REGARDING FEDERALLY SPONSORED RESEARCH OR DEVELOPMENT

The invention described herein includes contributions by one or more employees of the Department of the Navy made in performance of official duties and may be manufactured, used and licensed by or for the United States Government for any governmental purpose without payment of any royalties thereon. This invention (Navy Case 200548U503) is assigned to the United States Government and is available for licensing for commercial purposes. Licensing and technical inquiries may be directed to the Technology Transfer Office, Naval Surface Warfare Center Crane, email: Cran_CTO@navy.mil.

FIELD OF THE INVENTION

The present invention relates to a junctional tourniquet for treating junctional hemorrhages.

BACKGROUND AND SUMMARY OF THE INVENTION

The present invention relates to a junctional tourniquet that can used to treat a patient suffering from a junctional hemorrhage. A junctional hemorrhage is an externally compressible hemorrhage for which a standard extremity tourniquet with circumferential compression is ineffective. The anatomic junctions include the proximal groin, gluteal and pelvic regions, axilla and shoulder girdle, and the base of the neck. These are multidimensional dynamic joints with rotational forces and musculoskeletal anatomy preventing basic circumferential tourniquet compression. Circumferential compression is highly effective for peripheral-extremity injuries and has significantly reduced preventable fatalities due to hemorrhage. Because junctional hemorrhages cannot be effectively treated with circumferential compression, a specialized junctional tourniquet is required. Commercial junctional tourniquets are large, heavy, and costly to produce, making them unsuitable for field usage.

According to an illustrative embodiment of the present disclosure, a tourniquet has an inverted cone shape, wherein a narrower end has a mushroom shaped base that is pressed against a compression target and a broader end has a plurality of pass-through slots for straps.

According to a further illustrative embodiment of the present disclosure, a tourniquet has a broad plate component and a handle component. The handle component has a mushroom shaped base on a first end and a handle on a second end. The handle component passes through the center of the plate component with threads that allow the handle component to compress a target by twisting the handle.

Both tourniquets can be 3-D printed for approximately 10 U.S. dollars in resin. Mass production using injection molding would likely make them even more economical to produce. Because both tourniquets can use existing limb tourniquets, they can be wrapped around the patient with minimal movement of the patient.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which.

DETAILED DESCRIPTION OF THE DRAWINGS

The embodiments of the invention described herein are not intended to be exhaustive or to limit the invention to precise forms disclosed. Rather, the embodiments selected for description have been chosen to enable one skilled in the art to practice the invention.

Figure 1A:
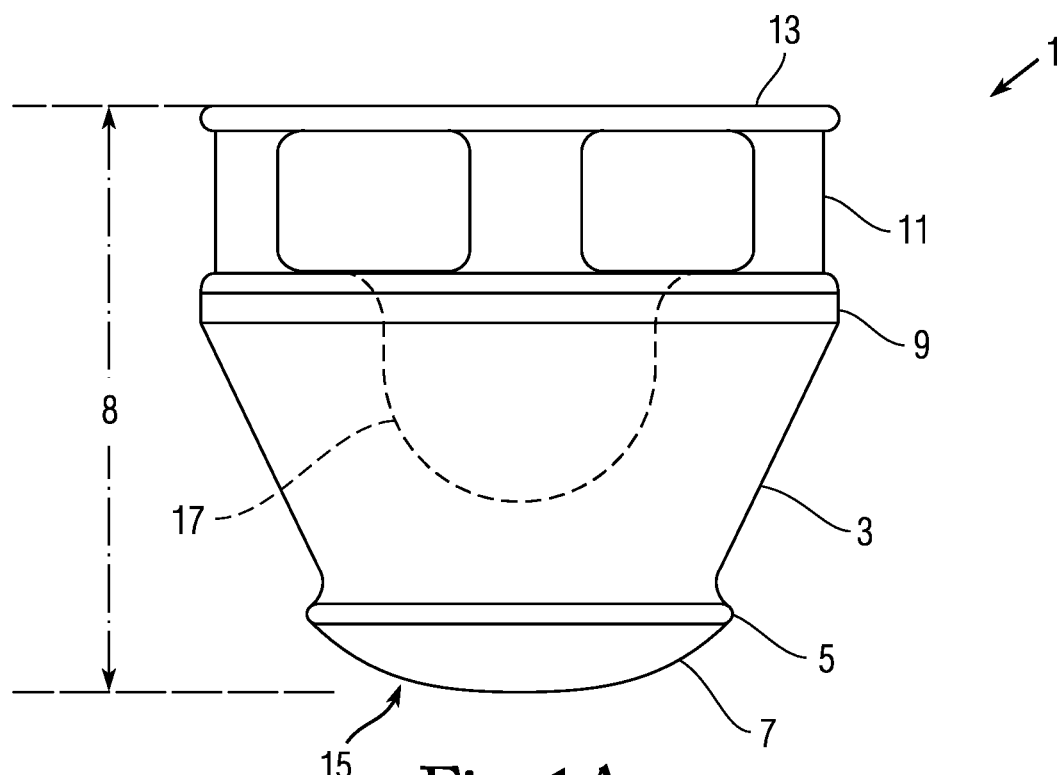
FIG. 1A shows a profile view of an exemplary tourniquet.

FIG. 1A shows a profile view of an exemplary tourniquet 1. The base diameter 5 (e.g., 46 millimeters (mm)) is smaller than the top diameter 9 (e.g., 70 mm). A smaller base allows the pressure to be focused in a smaller spot. This means less force is needed to compress a junction, for example the common femoral artery (CFA), with the desired results. The shape allows the tourniquet 1 to avoid obstructions such as bone, tissue, and organs so that the tourniquet 1 can properly compress the junction. The shape's ability to be pressed into the body helps to stabilize it and prevent tipping over. The exact cone angle 3 is not critical but will change the ratio of height to width. The mushroom style base 7 is able to apply pressure to a small area without digging or piercing the body. The base 7 includes a small flat spot 15 on the bottom (e.g., with a diameter of 10 mm). When placing a junctional tourniquet in the field, it may be difficult for the medic to precisely place the junctional tourniquet in the most effective location. The mushroom base shape allows for slight positioning errors while still effectively compressing the junction to the desired effect. The wide top with pass through slots (e.g., 14 mm tall) provide a stable platform when tightening with tourniquets. There are three support pillars 11. The top allows for off angle tourniquets to be applied. The ability to place tourniquets at multiple angles provides for enhanced stability in multiple axes. The ring 13 at the top prevents the tourniquets from slipping off. Slots can be added to the ring 13 itself to slip a strap (e.g., a limb tourniquet) through the ring 13. Increasing the height of the tourniquet 1 will increase the compression force, but decrease stability. A height of 64 mm can be used for the tourniquet 1 to balance compression force and stability. A cavity 17 can be added to reduce weight and material used. The material used to make the tourniquet 1 can vary, but it needs to withstand compression loads and field use.

Figure 1B:
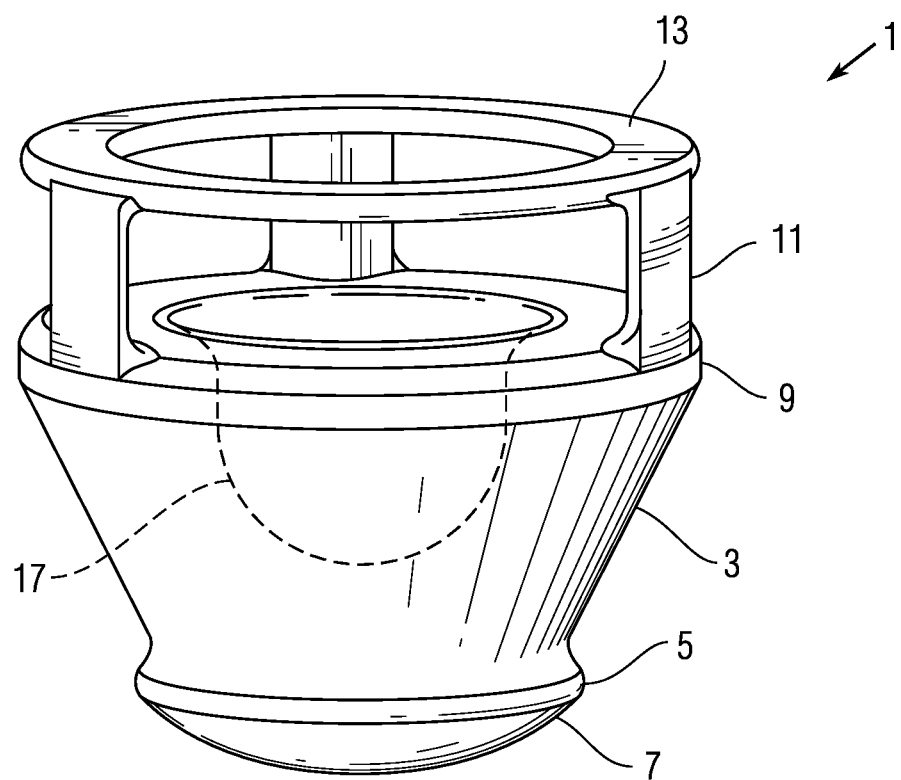
FIG. 1B shows an isometric view of an exemplary tourniquet.

FIG. 1B shows an isometric view of an exemplary tourniquet 1.

Figure 2A:
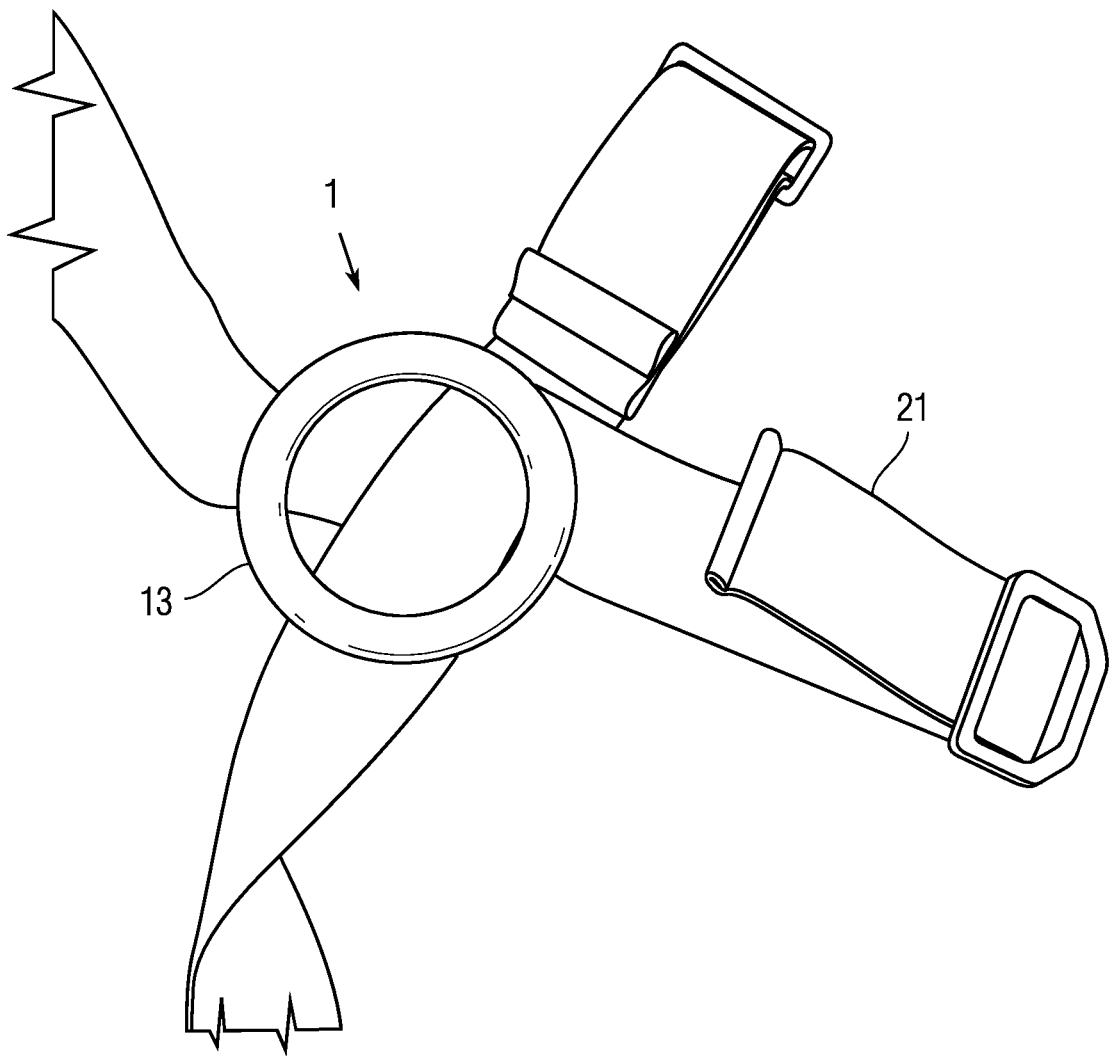
FIG. 2A shows an exemplary tourniquet with tourniquet straps.

FIG. 2A shows an exemplary tourniquet 1 with tourniquet straps 21. Use of the tourniquet 1 with a tourniquet 21 that has a locking windlass is preferred. However, any strap with a tightening feature could be used to apply pressure to the tourniquet 1 to compress the junction.

Figure 2B:
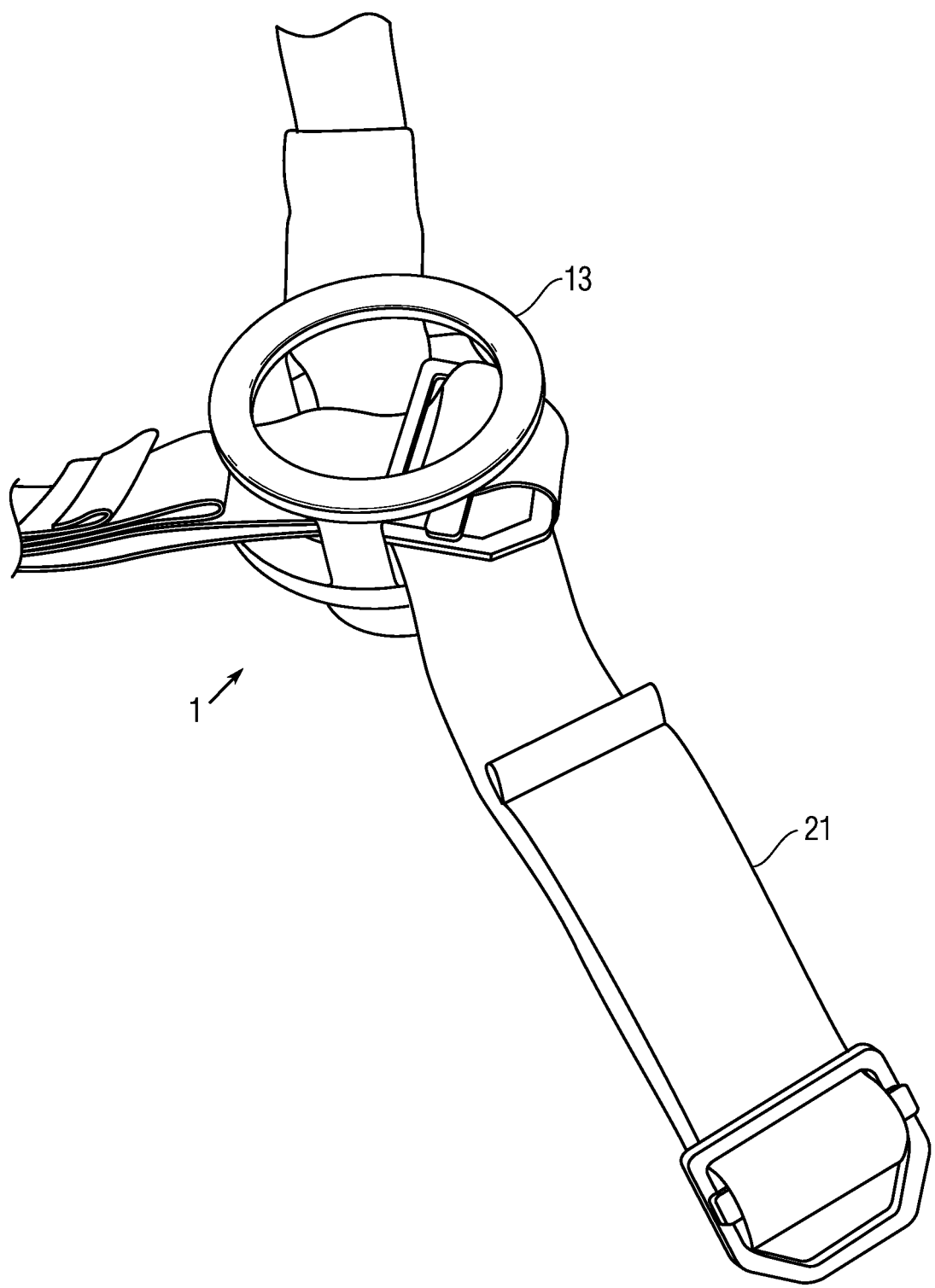
FIG. 2B shows an exemplary tourniquet with tourniquet straps.

FIG. 2B shows an exemplary tourniquet 1 with tourniquet straps 21.

Figure 2C:
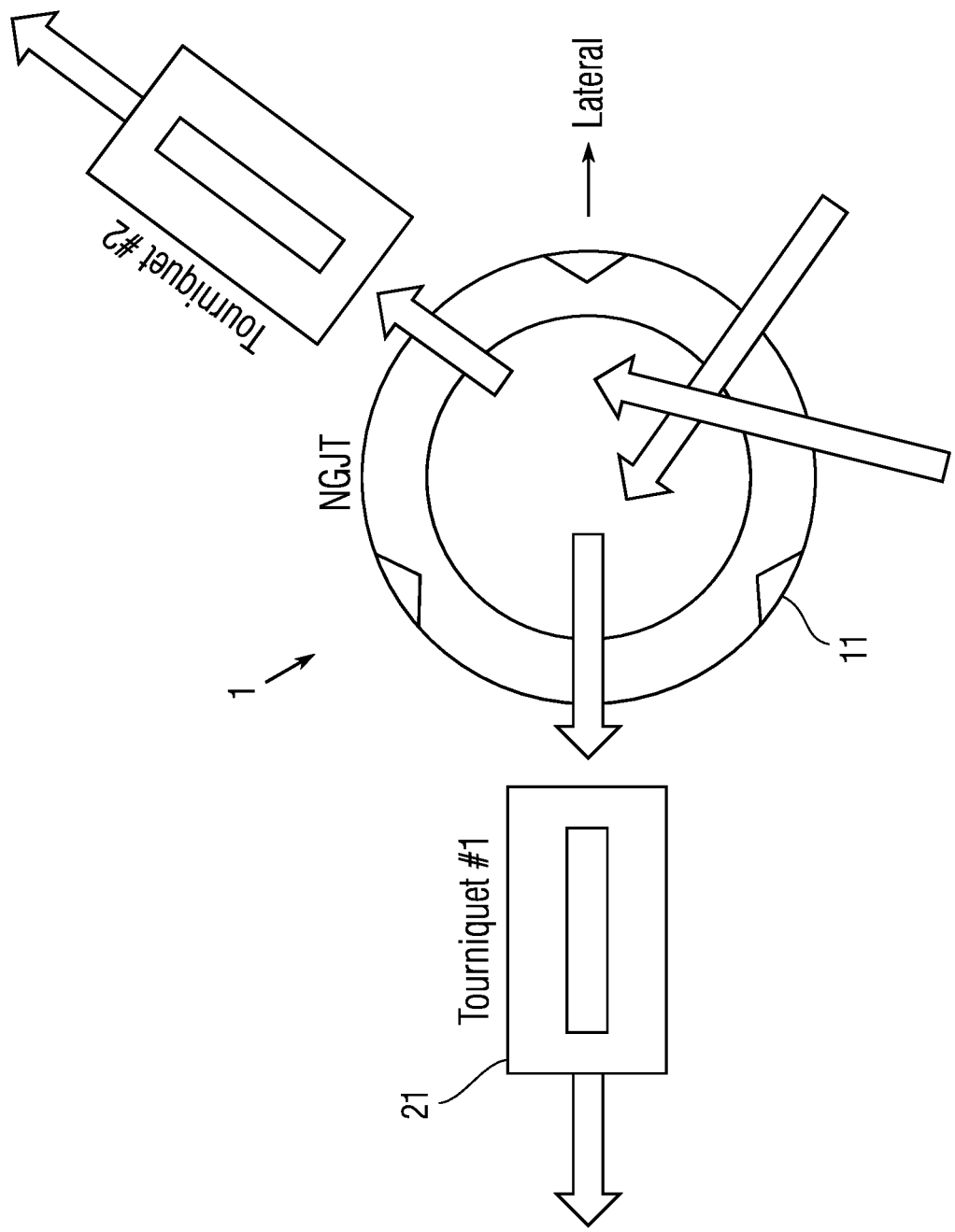
FIG. 2C shows a simplified view of an exemplary tourniquet with straps.

FIG. 2C shows a simplified view of an exemplary tourniquet 1 with tourniquet straps 21.

Figure 3A:
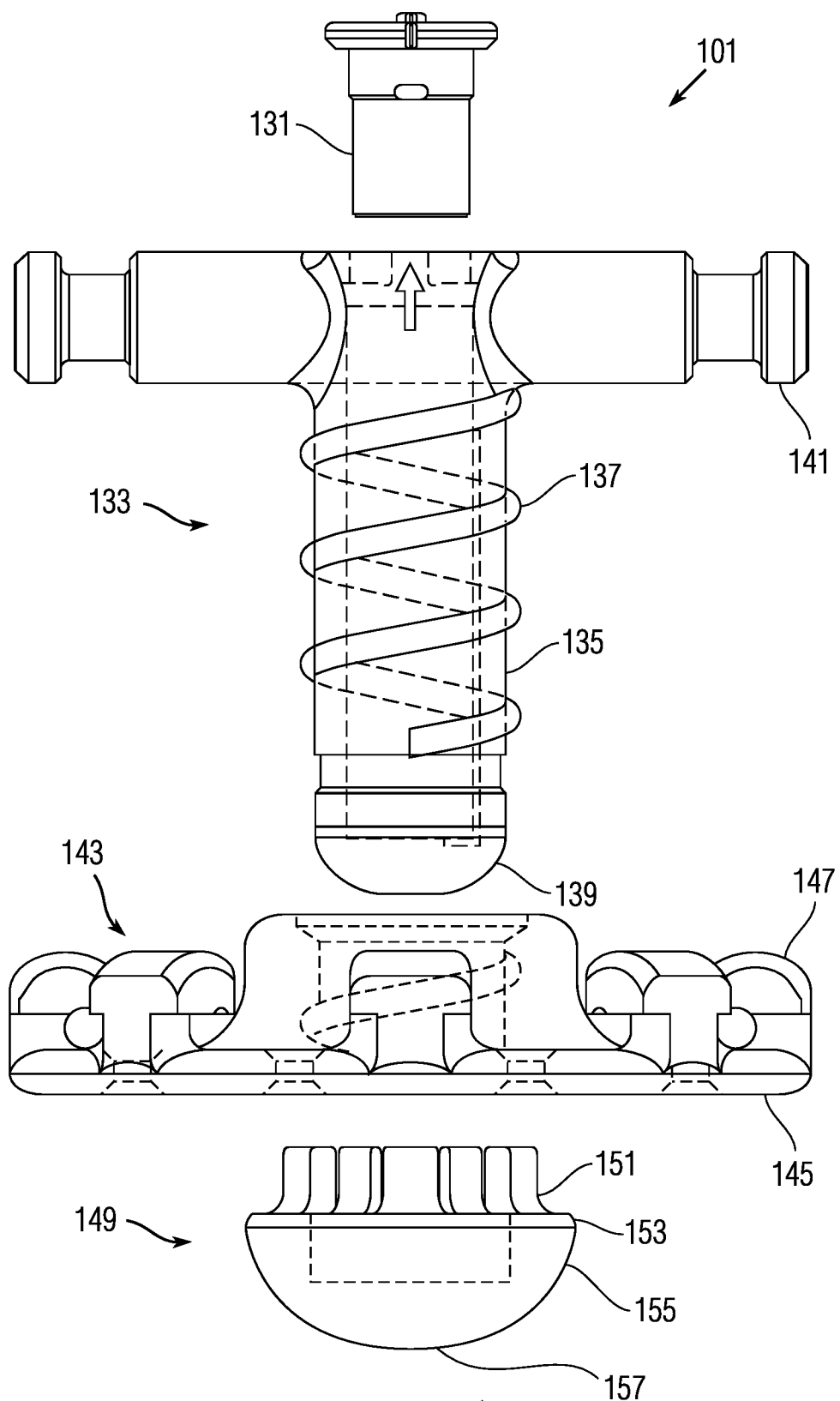
FIG. 3A shows an exploded view of an exemplary tourniquet.

FIG. 3A shows an exploded view of an exemplary tourniquet 101. The body section 135 of screw section 133 couples to a top plate 143 with threads 137. A base 149 is coupled to a bottom end of body section 135 such that rotating screw section 133 to lower/raise base 149 increases/decreases force and pressure applied to a junction. The base rim 151 is designed to snap onto the body section 135 and is able to rotate. Allowing the base rim 151 to rotate prevents the base 149 from twisting the skin and prevents it from walking-off. The diameter of base top section 153 (e.g., 50 mm diameter) is smaller than the diameter of top plate ring 145 (e.g., 120 mm) to allow the force to be focused in a smaller spot and decrease the force needed to compress the junction with the desired results. The curved shape of base 149 allows the tourniquet 101 to avoid obstructions such as bone, tissue, and organs so that the tourniquet 101 can properly compress the junction. The shape's ability to be pressed into the body helps to stabilize it and prevent tipping over. Second, the mushroom style base is able to apply pressure to a small area without digging or piercing the body. The base curves with a midpoint 155 (e.g., 40 mm diameter) with a small flat bottom 157 (e.g., 10 mm diameter). When placing a junctional tourniquet in the field, it may be difficult for a medic to precisely place the junctional tourniquet in the most effective location. The curved base shape allows for slight positioning errors while still effectively compressing the junction to the desired effect. The wide top plate ring 145 can include attachment posts 147 and holes (as shown in FIG. 3C) to secure the tourniquets or straps. The attachment posts 147 are designed to hook buckles around and prevent them from easily falling off. The holes can be used to secure the screw handle to prevent loosening or to attach the tourniquets. Multiple posts and holes allows the tourniquets to be applied at multiple angles. The ability to place tourniquets at multiple angles provides for enhanced stability in multiple axes. A handle section 141 can be used to facilitate rotation and provide additional compression to the junction. Grooves can be added to the handle to secure and prevent loosening. The screw thread height can be adjusted. To minimize storage in a field kit, the screw length can be equal to the diameter of base top section 153 (e.g., 50 mm). A low thread per inch can be selected for quick tightening and loosening. Body section 135 can be formed with a cavity provide a storage area. A cavity cap 131 can be used to close the cavity. The screw end 139 can be rounded to act as compression surface if the base 149 is lost in the field. Blood flow can be easily started and stopped again by rotating the screw section 133. This has the benefit of allowing the medic to back off the screw to start blood flow to identify hemorrhage locations if they need to convert the tourniquet. The material used to make the tourniquet 101 can vary, but it needs to withstand compression loads and field use. The screw shaft can indexed with a one-way ratchet to lock it at depth of insertion. The user can release this by pressing on the ratchet if subsequently attempting to convert the tourniquet.

Figure 3B:
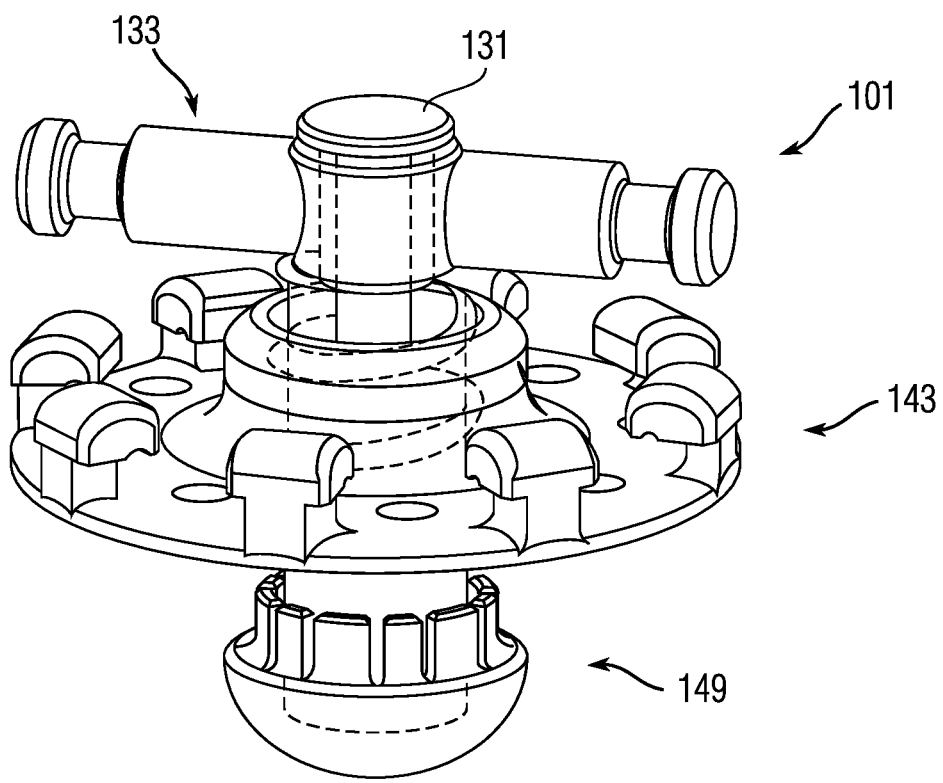
FIG. 3B shows an isometric view of an exemplary tourniquet.
Figure 3C:
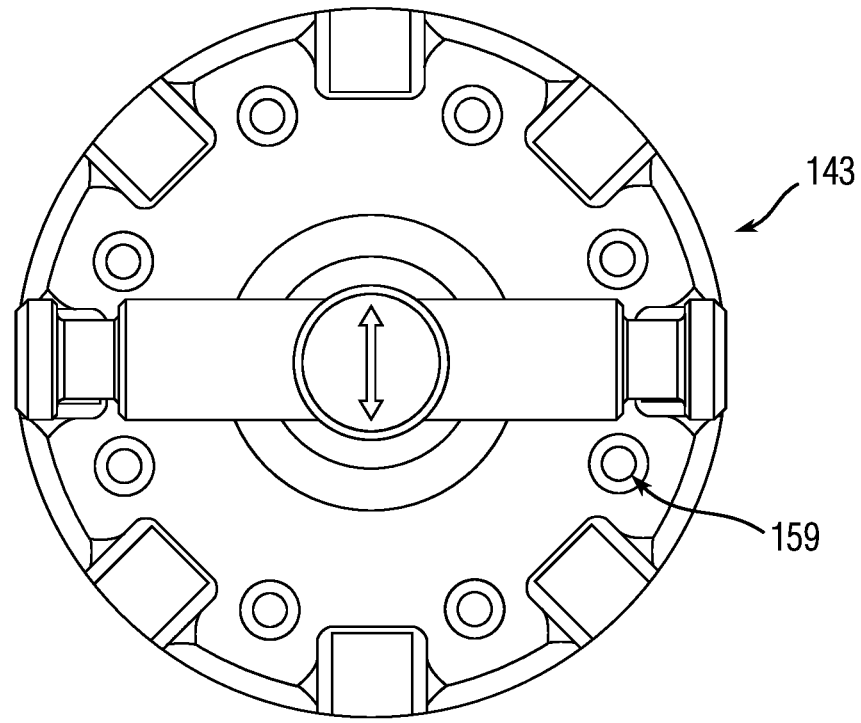
FIG. 3C shows a top down view of an exemplary tourniquet.

FIG. 3B shows an isometric view of an exemplary tourniquet 101. Use of the tourniquet 101 with a tourniquet 21 that has a locking windlass is preferred. However, any strap with a tightening feature could be used to apply pressure to the tourniquet 101 to compress the junction.

FIG. 3C shows a top down view of an exemplary tourniquet 101.

Figure 4A:
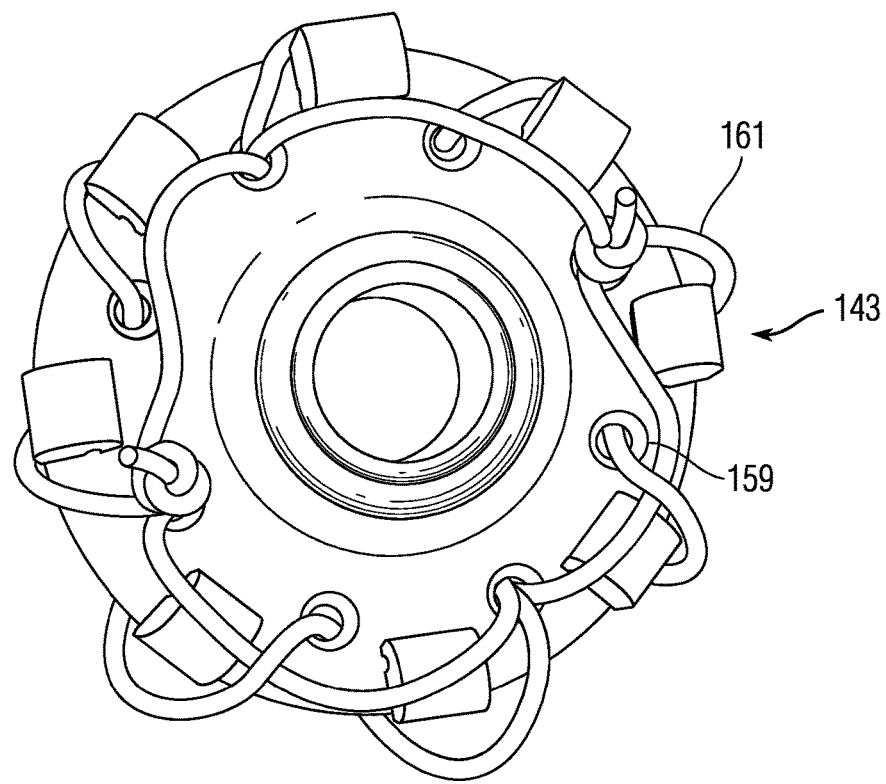
FIG. 4A shows an exemplary plate section.

FIG. 4A shows an exemplary plate section 143 with securing lines 161 passing through holes 159.

Figure 4B:
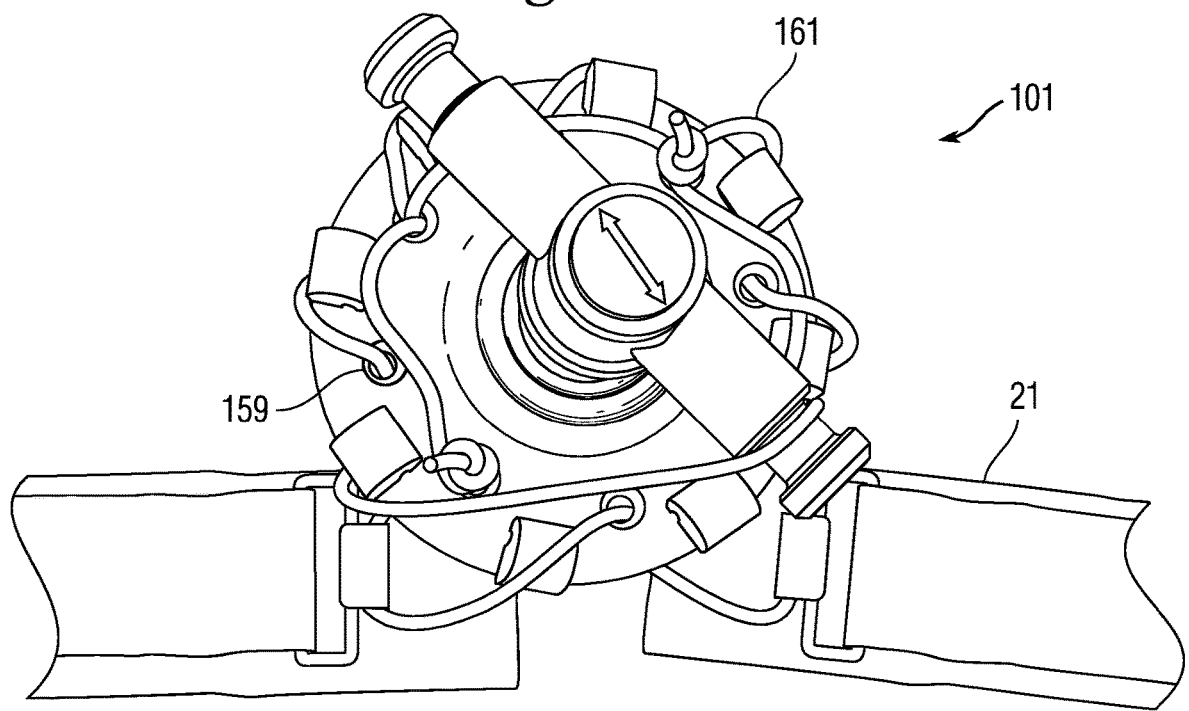
FIG. 4B shows an exemplary tourniquet with tourniquet straps.

FIG. 4B shows an exemplary tourniquet 101. Securing lines 161 pass through holes 159 to couple tourniquet 101 to tourniquet straps 21.

Figure 5A:
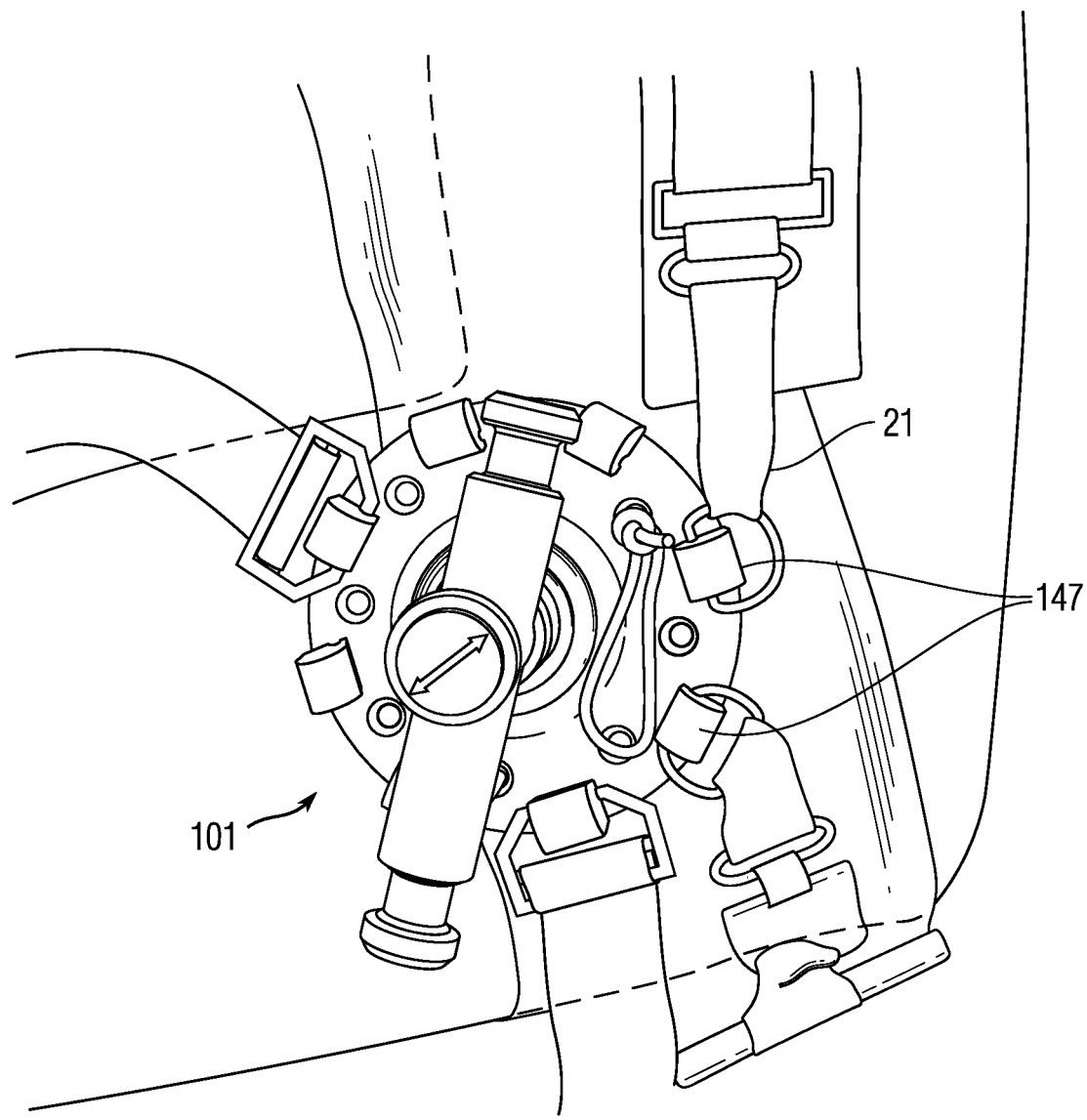
FIG. 5A shows an exemplary tourniquet in an operational setting.

FIG. 5A shows an exemplary tourniquet 101 in use around a patient's thigh. Tourniquet straps 21 are coupled to attachment posts 147.

Figure 5B:
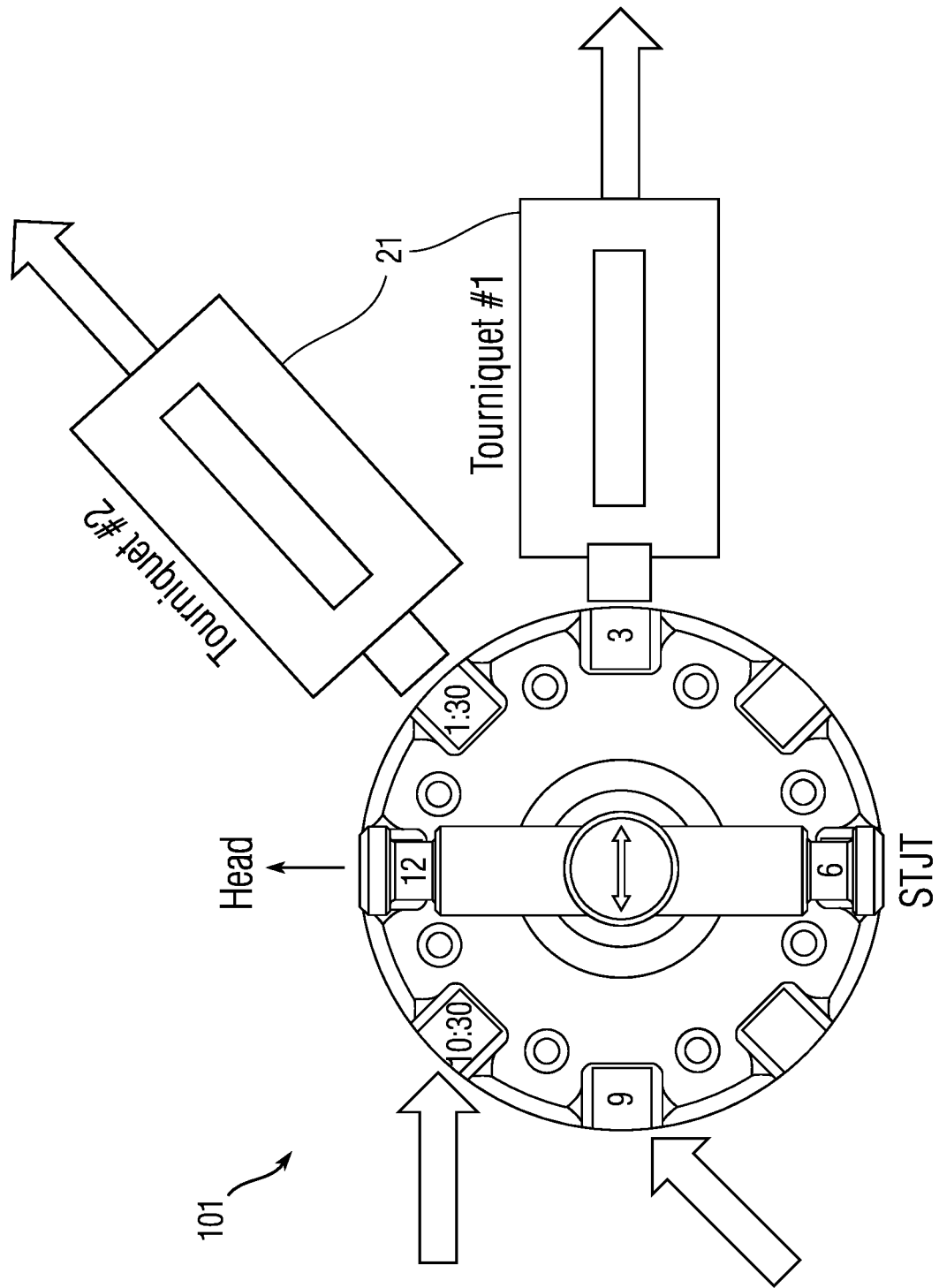
FIG. 5B shows a simplified view of an exemplary tourniquet with tourniquet straps.

FIG. 5B shows a simplified view of an exemplary tourniquet 101 with tourniquet straps 21.

Figure 6:
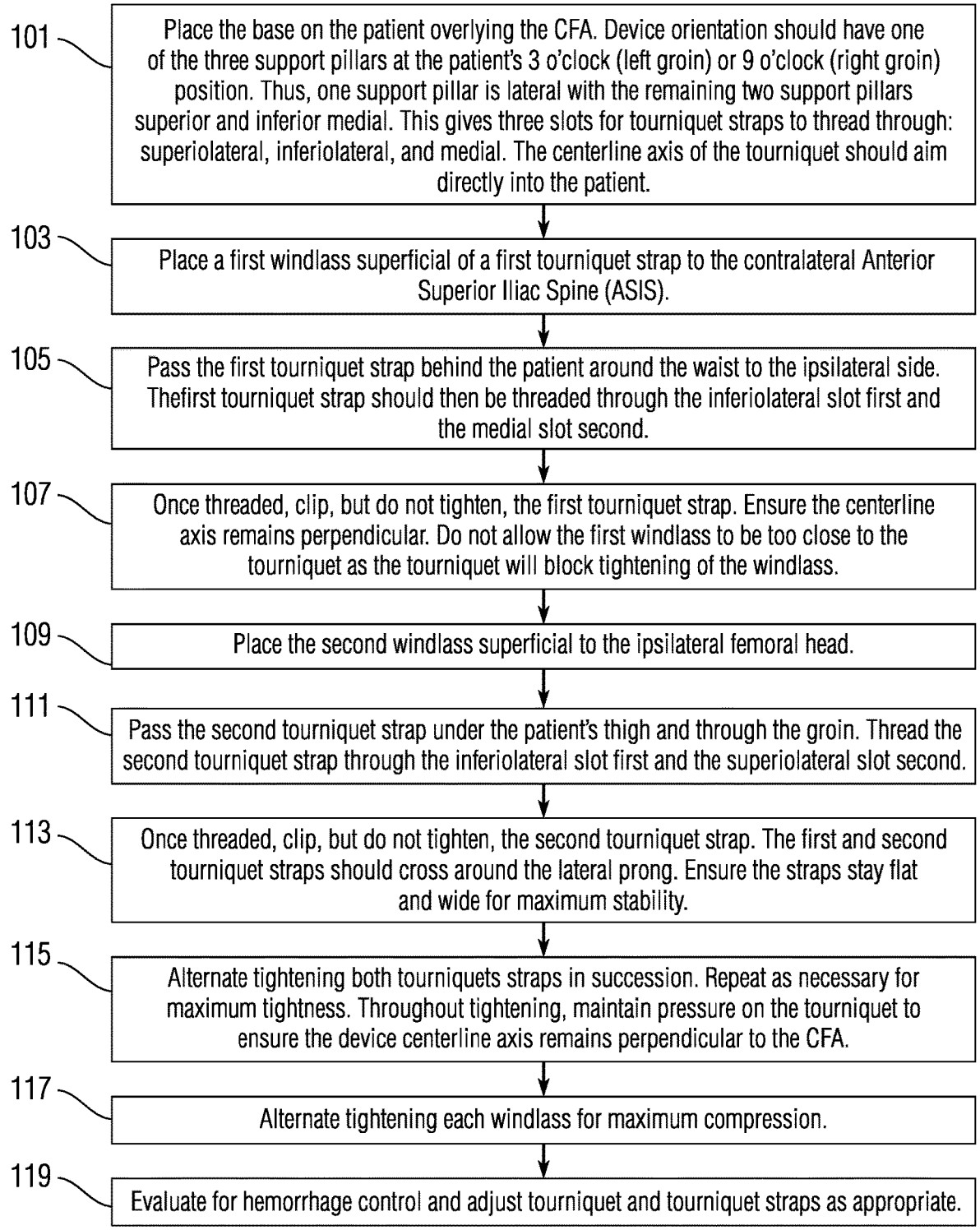
FIG. 6 shows an exemplary method of using a tourniquet.

FIG. 6 shows an exemplary method of using a tourniquet 1, such as that shown in FIGS. 1A-1B, to constrict a CFA. At Step 101: Place the base on the patient overlying the CFA. Device orientation should have one of the three support pillars at the patient's 3 o'clock (left groin) or 9 o'clock (right groin) position. Thus, one support pillar is lateral with the remaining two support pillars superior and inferior medial. This gives three slots for tourniquet straps to thread through: superiolateral, inferiolateral, and medial. The centerline axis of the tourniquet should aim directly into the patient. At Step 103: Place a first windlass superficial of a first tourniquet strap to the contralateral Anterior Superior Iliac Spine (ASIS). At Step 105: Pass the strap behind the patient around the waist to the ipsilateral side. The first tourniquet strap should then be threaded through the inferiolateral slot first and the medial slot second. At Step 107: Once threaded, clip, but do not tighten, the first tourniquet strap. Ensure the centerline axis remains perpendicular. Do not allow the first windlass to be too close to the tourniquet as the tourniquet will block tightening of the windlass. At Step 109: Place the second windlass superficial to the ipsilateral femoral head. At Step 111: Pass the second tourniquet strap under the patient's thigh and through the groin. Thread the second tourniquet strap through the inferiolateral slot first and the superiolateral slot second. At Step 113: Once threaded, clip, but do not tighten, the second tourniquet strap. The first and second tourniquet straps should cross around the lateral prong. Ensure the straps stay flat and wide for maximum stability. At Step 115: Alternate tightening both tourniquets straps in succession. Repeat as necessary for maximum tightness. Throughout tightening, maintain pressure on the tourniquet to ensure the device centerline axis remains perpendicular to the CFA. At Step 117: Alternate tightening each windlass for maximum compression. At Step 119: Evaluate for hemorrhage control and adjust tourniquet and tourniquet straps as appropriate.

Figure 7:
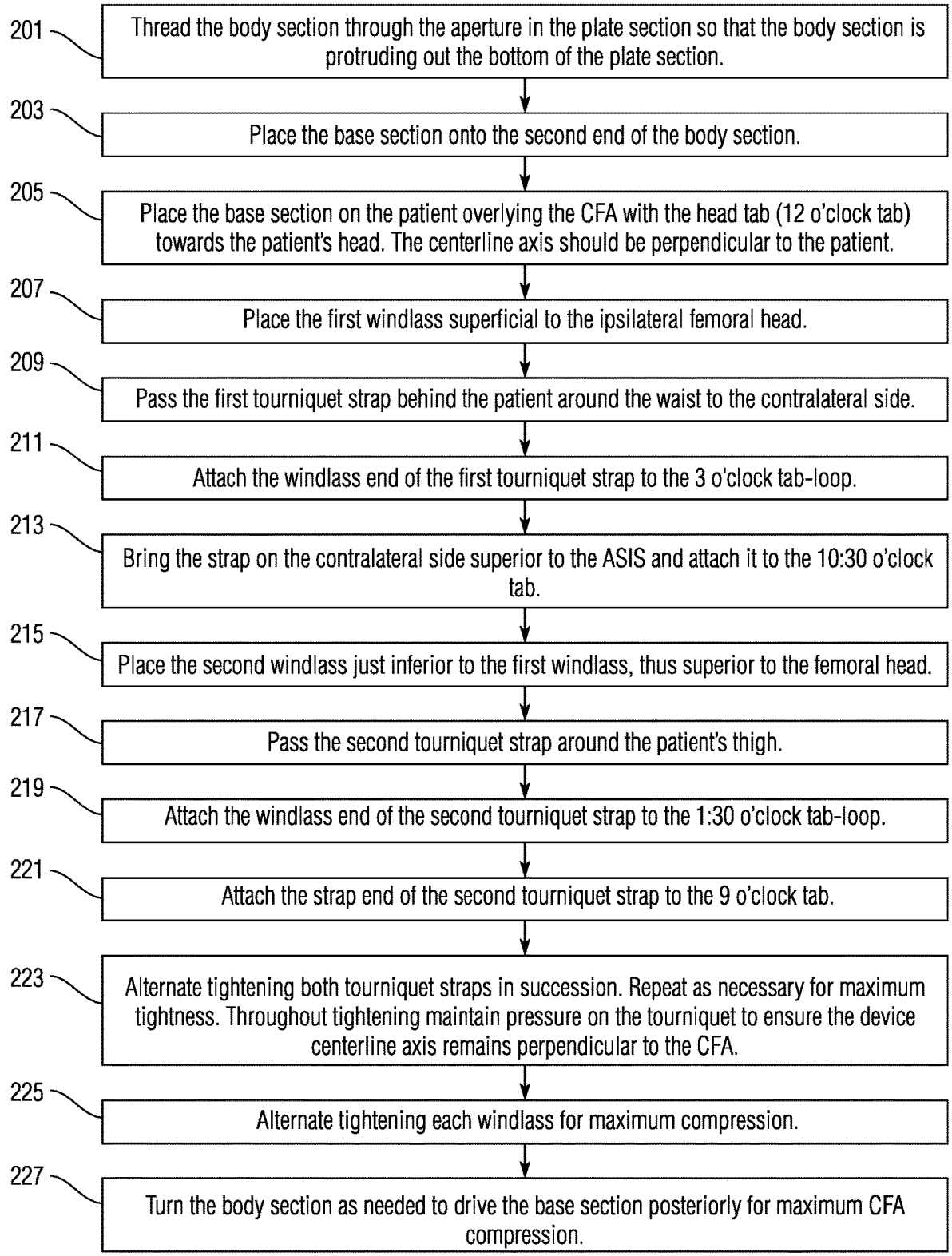
FIG. 7 shows another exemplary method of using a tourniquet.

FIG. 7 shows an exemplary method of using a tourniquet 101, such as that shown in FIGS. 3A-3C, to constrict a CFA. Step 201: Thread the body section through the aperture in the plate section so that the body section is protruding out the bottom of the plate section. At Step 203: Place the base section onto the second end of the body section. At Step 205: Place the base section on the patient overlying the CFA with the head tab (12 o'clock tab) towards the patient's head. The centerline axis should be perpendicular to the patient. At Step 207: Place the first windlass superficial to the ipsilateral femoral head. At Step 209: Pass the first tourniquet strap behind the patient around the waist to the contralateral side. At Step 211: Attach the windlass end of the first tourniquet strap to the 3 o'clock tab-loop. At Step 213: Bring the strap on the contralateral side superior to the ASIS and attach it to the 10:30 o'clock tab. Do not tighten yet. At Step 215: Place the second windlass just inferior to the first windlass, thus superior to the femoral head. At Step 217: Pass the second tourniquet strap around the patient's thigh. At Step 219: Attach the windlass end of the second tourniquet strap to the 1:30 o'clock tab-loop. At Step 221: Attach the strap end of the second tourniquet strap to the 9 o'clock tab. At Step 223: Alternate tightening both tourniquet straps in succession. Repeat as necessary for maximum tightness. Throughout tightening, maintain pressure on the tourniquet to ensure the device centerline axis remains perpendicular to the CFA. At Step 225: Alternate tightening each windlass for maximum compression. At Step 227: Turn the body section as needed to drive the base section posteriorly for maximum CFA compression.

Although the invention has been described in detail with reference to certain preferred embodiments, variations and modifications exist within the spirit and scope of the invention as described and defined in the following claims.

The invention claimed is:

1. A junctional tourniquet comprising:
a circular top plate ring, wherein the top plate ring is formed with a central first aperture, wherein an inner surface of the central first aperture is formed with a first plurality of threads;
a body section comprising a cylinder and a handle section coupled to a first end of the cylinder, wherein the body section is formed with a second plurality of threads on an outer surface of the cylinder, wherein the body section is coupled to the top plate ring by the first and second pluralities of threads;
a base section, wherein a first end of the base section is coupled to a second end of the body section, wherein a second end of the base section is formed with a first curved edge and a first flat circular surface;
a first attachment means comprising a plurality of attachment posts rising above the circular top plate ring, away from the base section, and radially spaced around the circular top plate ring;
a second attachment means comprising a plurality of holes radially spaced around the circular top plate ring and securing lines that pass through the plurality of holes;
one or more first tourniquet straps that attach to the attachment post; and
one or more second tourniquet straps that attach to the securing line.

2. The junctional tourniquet of claim 1, further comprising:
a cap section;
wherein the body section forms a cavity and forms a second aperture on the first end of the cylinder such that the second aperture opens into the cavity;
wherein the cap section is configured to couple to the second aperture.

3. The junctional tourniquet of claim 1, wherein the top plate ring forms a plurality of apertures each connecting a first side of the top plate ring to a second side of the top plate ring.

4. The junctional tourniquet of claim 1, wherein the second end of the body section is formed with a second curved edge and a second flat circular surface.

5. The junctional tourniquet of claim 1, wherein a diameter of the base section is smaller than the top plate ring to concentrate force from the base section into a smaller area to cause a decrease in force needed to compress a junction.

6. The junctional tourniquet of claim 3, wherein the plurality of attachment posts and apertures secure the tourniquet to one or more of a plurality of straps.

7. The junctional tourniquet of claim 1, wherein the handle section facilitates rotation and provides additional compression to a junction.

8. The junctional tourniquet of claim 1, further comprising an indexed screw shaft with a one-way ratchet to lock the body section at depth of insertion.

* * * * *